US006548051B2

(12) United States Patent
Garnier et al.

(10) Patent No.: US 6,548,051 B2
(45) Date of Patent: Apr. 15, 2003

(54) HAIR STYLING COMPOSITION COMPRISING ADHESIVE PARTICLES

(75) Inventors: Nathalie Garnier, Scotch Plains, NJ (US); Henri Samain, Bièvres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/930,187

(22) Filed: Aug. 16, 2001

(65) Prior Publication Data

US 2002/0041858 A1 Apr. 11, 2002

Related U.S. Application Data

(60) Provisional application No. 60/225,644, filed on Aug. 16, 2000, and provisional application No. 60/229,306, filed on Sep. 1, 2000.

(51) Int. Cl.⁷ ................................. A61K 7/06
(52) U.S. Cl. .................. 424/70.1; 424/401; 424/489
(58) Field of Search ..................... 424/401, 70.1, 424/70.11, 70.16, 70.21, 70.22, 70.27, 70.31, 489, 490

(56) References Cited

U.S. PATENT DOCUMENTS

| 2,047,398 A | 7/1936 | Voss et al. |
|---|---|---|
| 2,723,248 A | 11/1955 | Wright |
| 3,716,633 A | 2/1973 | Viout et al. |
| 3,810,977 A | 5/1974 | Levine et al. |
| 3,836,537 A | 9/1974 | Boerwinkle et al. |
| 3,946,749 A | 3/1976 | Papantoniou |
| 3,966,403 A | 6/1976 | Papantoniou et al. |
| 4,031,307 A | 6/1977 | DeMartino et al. |
| 4,070,533 A | 1/1978 | Papantoniou et al. |
| 4,128,631 A | 12/1978 | Lundmark et al. |
| 4,131,576 A | 12/1978 | Iovine et al. |
| 4,137,208 A | 1/1979 | Elliott |
| 4,165,367 A | 8/1979 | Chakrbarti |
| 4,282,203 A | 8/1981 | Jacquet et al. |
| 4,289,752 A | 9/1981 | Mahieu et al. |
| 4,693,935 A | 9/1987 | Mazurek |
| 4,728,571 A | 3/1988 | Clemens et al. |
| 4,963,348 A | 10/1990 | Bolich, Jr. et al. |
| 4,972,037 A | 11/1990 | Garbe et al. |
| 5,019,377 A | 5/1991 | Torgerson |
| 5,538,717 A | 7/1996 | La Poterie |
| 5,565,193 A | 10/1996 | Midha et al. |
| 6,106,813 A | 8/2000 | Mondet et al. |
| 6,166,093 A | 12/2000 | Mougin et al. |
| 6,346,234 B1 | 2/2002 | Rollat et al. |
| 6,372,876 B1 | 4/2002 | Kim et al. |
| 6,395,265 B1 | 5/2002 | Mougin et al. |

FOREIGN PATENT DOCUMENTS

| DE | 2330956 | 1/1974 |
|---|---|---|
| EP | 0080976 | 6/1983 |
| EP | 0412704 | 2/1991 |
| EP | 0582152 | 2/1994 |
| EP | 0619111 | 10/1994 |
| EP | 0637600 | 2/1995 |
| EP | 0648485 | 4/1995 |
| EP | 0656021 | 6/1995 |
| EP | 0751162 | 1/1997 |
| EP | 0412707 | 2/1997 |
| FR | 1222944 | 6/1960 |
| FR | 1400366 | 4/1965 |
| FR | 1564110 | 3/1969 |
| FR | 1580545 | 9/1969 |
| FR | 2077143 | 10/1971 |
| FR | 2198719 | 4/1974 |
| FR | 2265781 | 10/1975 |
| FR | 2265782 | 10/1975 |
| FR | 2350384 | 12/1977 |
| FR | 2357241 | 2/1978 |
| FR | 2393573 | 1/1979 |
| FR | 2439798 | 5/1980 |
| FR | 2743297 | 7/1997 |
| GB | 839805 | 6/1960 |
| LU | 75370 | 2/1978 |
| LU | 75371 | 2/1978 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 96/32920 | 10/1996 |
| WO | WO 98/38969 | 9/1998 |
| WO | WO98/38969 | * 9/1998 |
| WO | WO98/48770 | * 11/1998 |
| WO | WO 98/48770 | 11/1998 |
| WO | WO 98/48771 | 11/1998 |
| WO | WO 98/48772 | 11/1998 |
| WO | WO 98/49213 | 11/1998 |
| WO | WO 98/51276 | 11/1998 |
| WO | WO 98/53794 | 12/1998 |
| WO | WO 99/00105 | 1/1999 |

OTHER PUBLICATIONS

Title: Hair Styling Composition Comprising Encapsulated Adhesives, By: Nathalie Garnier and Henri Samain, Filed: Aug. 16, 2001, Application No.: 09/930,253, Attorney Docket No.: 05725.0596–00000.

Clyde Orr, "Size Measurement of Particles," *Kirk–Othmer: Encyclopedia of Chemical Technology*, vol. 21, pp. 106–131 (3rd ed. 1983).

* cited by examiner

*Primary Examiner*—Jose' G. Dees
*Assistant Examiner*—Konata M. George
(74) *Attorney, Agent, or Firm*—Finnegan, Henderson, Farabow, Garrett & Dunner, L.L.P.

(57) ABSTRACT

Hair styling compositions that comprise at least one adhesive particle, optionally in a cosmetically acceptable carrier, wherein said at least one adhesive particle comprises at least one substrate and an at least partial coating, wherein said at least partial coating comprises at least one adhesive, wherein the at least one substrate and the at least partial coating are not the same, and wherein the at least one adhesive particle has a mean length greater than 1 micron. The present invention also relates to methods of providing a holding and/or reshapable effect to the hair using the compositions of the invention and methods of manufacturing of said compositions.

71 Claims, No Drawings

HAIR STYLING COMPOSITION COMPRISING ADHESIVE PARTICLES

This application claims benefit to Provisional Application No. 60/225,644 filed Aug. 16, 2000 and Provisional Application No. 60/229,306 filed Sep. 1, 2000.

The present invention is directed to compositions and methods for styling hair. More particularly, the hair styling compositions of the present invention comprise at least one adhesive particle optionally in a cosmetically acceptable carrier. The compositions of the present invention may have at least one adhesive particle present in an amount effective to provide a holding and/or reshapable effect.

Fixing the hairstyle is an important element in hair styling, and involves, for example, maintaining a shaping that has already been carried out, or simultaneously shaping and fixing of the hair.

In accordance with the invention, the term "hair styling composition" relates to any kind of composition that can be used to effect hair styling including, for example, fixing compositions, shampoos, conditioners, permanent waving compositions, hair care products, and hair treatment products.

There are countless products available to the consumer, which enable one to style his/her hair in a particular shape or configuration and result in the desired shape or configuration being retained. The holding or retention of the style is usually accomplished by the delivery of a composition containing a film former or an adhesive that remains on the hair after evaporation of some or all of the carrier. As used herein, the term "carrier" refers to any solvent or other cosmetically acceptable formulation that is useful in delivering a cosmetic agent as described below.

The most prevalent hair styling compositions on the cosmetic market for shaping and/or fixing the hairstyle are spray compositions comprising a carrier, usually alcohol- or water-based, and one or more materials, generally polymer resins. One of the functions of a polymer resin is to form links between the hairs, these materials also being called fixatives, in a mixture with various cosmetic adjuvants. This solution is generally packaged either in an appropriate aerosol container, which is pressurized with the aid of a propellant, or in a pump flask.

Other known hair styling compositions include styling gels and mousses, which are generally applied to the wetted hair before brushing or setting it. In contrast to the conventional aerosol lacquers, these compositions can have the disadvantage that they do not allow the hair to be fixed in a shape created before their application. In fact, these compositions are essentially aqueous and their application wets the hair, rendering it difficult to maintain the initial shape of the hairstyle. In order to shape and fix the hairstyle, therefore, it is necessary to carry out subsequent brushing and/or drying with these types of compositions.

One embodiment of the present invention provides a hair styling composition comprising, optionally in a cosmetically acceptable carrier, at least one adhesive particle, wherein the at least one adhesive particle comprises at least one substrate and an at least partial coating, wherein the at least partial coating comprises at least one adhesive.

The invention further provides for a method of providing a holding effect to the hair by applying to the hair a hair styling composition that comprises, optionally in a cosmetically acceptable carrier, at least one adhesive particle, wherein the at least one adhesive particle comprises at least one substrate and an at least partial coating, wherein the at least partial coating comprises at least one adhesive and wherein the at least one adhesive particle is present in an amount effective to provide a holding effect. The adhesive particle may retain its adhesive properties following evaporation of the cosmetically acceptable carrier.

As used herein, to provide a "holding effect" means to provide a hair styling that retains a desired shape or configuration until water, heat, time, and/or physical contact disrupt the means by which the desired shape or configuration had been retained.

While the hair styling compositions currently on the market are very effective in holding the hair in a desired shape or configuration, generally they are not designed to allow the hairstyle to be later modified to a desired shape, which is other than that formed initially, without reapplying a hair styling composition or heat. Moreover, under various kinds of stress, the hairstyle has a tendency to take on an undesirable permanent set, which cannot easily be modified. For example, as the carrier evaporates, bridging or welding points are formed between and among individual hair strands or groups of hair strands to maintain the desired shape. However, those bridges or weld points may be easily broken by brushing, combing or other mechanical means, such as running one's fingers through the hair. Once broken, the weld points of such compositions cannot be reset and the styling or hold formerly maintained by the weld point is lost. Typically, the user's only recourse for restyling and holding the hair in a newly or previously desired style or configuration is to reapply such a hair styling composition or heat. Unfortunately, in addition to being bothersome, several re-applications of most hair styling compositions result in hair with a rough feel and texture and a stiff and unnatural look.

In attempts to provide a hair styling composition that may be reworked, a composition that applies a flexible film has been used with the hope that it would allow rearrangement of hair without impairing the hair holding capability. See WO 99/00105. This hair styling composition utilizes specific organic adhesive polymers in association with ethoxylated alcohol surfactants and a carrier. The composition can be delivered in the form of a mousse. Similarly, U.S. Pat. No. 5,019,377 describes a flexible film composition for a temporary arrangement of the hair, which comprises the use of a low glass transition temperature adhesive copolymer. At least one of the monomers making up the adhesive copolymer is selected from acrylate amides and methacrylate amides and at least one other monomer is selected from acrylate esters and methacrylate esters.

While the compositions described above result in flexible films that are effective in holding the hair and can allow some reworking of the hair, they are not yet optimized. Specifically, where weld points holding the hair together form and can encompass many strands or clumps of hair, the hair cannot be reworked with ease. This can give an unnatural effect to the hair, such as a helmet appearance. Additionally, these weld points, as in previous hair styling compositions, are easily broken. Once the weld points are broken, the hair cannot be reworked. Consequently, one embodiment of the present invention relates to hair styling compositions that do not rely on such non-reworkable weld points to retain a shape or configuration of the hair and therefore enable a shape or configuration to be easily and repeatedly reworked without re-application of the hair styling composition or heat.

In another embodiment, the present invention provides a reshapable hair styling composition comprising, optionally in a cosmetically acceptable carrier, at least one adhesive particle, wherein the at least one adhesive particle comprises at least one substrate and an at least partial coating, wherein the at least partial coating comprises at least one adhesive and wherein the at least one adhesive particle is present in an amount effective to obtain a reshapable effect.

The invention further provides for a method of providing a reshapable effect to the hair by applying to the hair a reshapable hair styling composition that comprises, optionally in a cosmetically acceptable carrier, at least one adhesive particle, wherein the at least one adhesive particle comprises at least one substrate and an at least partial coating, wherein the at least partial coating comprises at least one adhesive and wherein the at least one adhesive particle is present in an amount effective to provide a reshapable effect. The adhesive particle may retain its adhesive properties following evaporation of the cosmetically acceptable carrier.

The term "reshapable" hair styling composition means a hair styling composition providing hair styling that can be restored or modified without new material or heat being applied. For example, in order to restore or modify the hairstyle in case of "drooping" or loss of setting (dishevelment), no new materials, such as water or any form of fixing agent, or heat are required. Thus, to provide a "reshapable" effect means to provide a hair styling that can be restored or modified without new material or heat being applied. The efficacy of the composition can be long lasting, such as 10–24 hours, giving rise to a durable styling effect. Other terms, which may be synonymous with reshapable, include repositionable, remoldable, restyleable, rearrangable, and remodellable.

It is to be understood that both the foregoing general description and the following detailed description are exemplary and explanatory only and are not restrictive of the invention as claimed.

Reference will now be made in detail to exemplary embodiments of the present invention. The invention, in one aspect, provides a hair styling composition comprising, optionally in a cosmetically acceptable carrier, at least one adhesive particle, as set forth above. In another aspect, the invention provides a hair styling composition comprising, optionally in a cosmetically acceptable carrier, at least one adhesive particle, as set forth above, wherein the at least one adhesive particle is present in an amount effective to provide a holding effect. In yet another aspect, the invention provides a reshapable hair styling composition comprising, optionally in a cosmetically acceptable carrier, at least one adhesive particle, as set forth above, wherein the at least one adhesive particle is present in an amount effective to provide a reshapable effect. The invention also provides for methods of using and making these hair styling compositions.

Typically, hair styling compositions utilize liquid adhesives that lose all of their tack upon evaporation of the carrier. In other words, the adhesive bond or weld point is set when the carrier evaporates and cannot be reset or repositioned. Unexpectedly, it has been discovered that the use of adhesive particles may bring about superior qualities in the hold of the hair and/or the ability to reshape the hair with simple means.

As used herein, an "adhesive particle" is a coated discrete substrate, which comprises at least one substrate coated with an at least partial coating that comprises at least one adhesive, effective in providing a composition with a holding and/or reshapable effect. In one embodiment, the at least one adhesive particle remains tacky or sticky following evaporation of the carrier. It is not necessary for the at least one adhesive particle to be spherical or any particular shape, and there is no requirement that the at least one adhesive particle be solid or have a specific hardness. More specifically, an adhesive particle of the invention is either (a) a discrete substrate that is not an adhesive and is at least partially coated with a coating comprising at least one adhesive or (b) a discrete substrate that is formed from or comprises, in whole or in part, at least one adhesive and is also at least partially coated with a coating comprising at least one adhesive. In one embodiment, the at least one substrate and the at least partial coating comprise the same adhesive. In another embodiment, the at least one substrate and the at least partial coating do not comprise the same adhesive.

With respect to the at least partial coating comprising at least one adhesive, the thickness of the coat is not critical; however, the at least one adhesive particle is most effective if a substantial portion of the surface area of the particle is covered. An acceptable partial coating is one where the coating is present to a degree such that there is an effective amount of the at least one adhesive to adhere to keratinous fibers. As used herein, to be coated, whether partially or fully, means that at least part of the surface of the adhesive particle has adhesive properties due to the coating. One of ordinary skill in the art would recognize that an at least partial coating may comprise various layers and may comprise constituents other than the at least one adhesive. An at least partial coating comprising at least one adhesive may be achieved, for example, by the addition of at least one adhesive to at least part of the surface or the treatment of at least part of the surface of the at least one substrate by physical or chemical means, such that at least part of the surface is rendered adhesive.

As for the at least one substrate, the materials that could be used in the practice of the invention include adhesives and any particle, e.g., inert particle, that does not substantially decrease desired adhesive and/or reshapable properties of the at least partial coating comprising at least one adhesive. Representative inert substrates include, but are not limited to, polymeric materials, such as polyethylene, polypropylene, and polyacrylates; metal alloys; metal oxides; ceramics; and glasses. In one embodiment, each adhesive particle comprises a mix of ceramic and glass substrates at least partially coated by an adhesive. In another embodiment, both the at least one substrate and the at least one adhesive of the at least partial coating are the same adhesive. In yet another embodiment, the at least one substrate and the at least one adhesive of the at least partial coating are not the same adhesive. In yet a further embodiment, the at least one substrate and the at least partial coating are not the same, e.g., when both the at least one substrate and the at least partial coating each comprise the same adhesive, then either the at least one substrate or the at least partial coating, or both, must further comprise a suitable material not present in the other.

The size, shape, and/or the total surface area of the at least one adhesive particle can vary widely. It is helpful but not required for the at least one adhesive particle to possess a surface such that the strands of hair can position themselves along the surface and can touch the at least one adhesive of the coating. While not wishing to be bound by theory, the at least one adhesive particle, and even the particles of irregular shape, may offer enough surface area to allow for the hair or hair strands to be held together through a bridging by the at least one adhesive particle. For example, adhesive particles that have a long side and can position themselves with their long side parallel or substantially parallel to the hair, may bring about better holding and/or reshaping of the hair even after the hair has been already set or styled.

The at least one adhesive particle of the present invention may be of widely varied shapes such as spheres, spheroids, rods, platelets, flakes, and irregularly shaped particles. The size of the at least one substrate and/or at least one adhesive particle is usually described in terms of its length and/or width. In the context of the present invention, "length" of at least one substrate and/or at least one adhesive particle is intended to mean the maximum distance possible to be measured by appropriate microscopy techniques, between two opposing points of the substrate and/or particle. The "width" of the at least one substrate and/or at least one adhesive particle is intended to mean the minimum distance possible to be measured by appropriate microscopy techniques, between two opposing points of the substrate and/or particle.

In one embodiment, the at least one substrate and/or at least one adhesive particle has a ratio of length to width of greater than or equal to about 1:1.

In another embodiment, the at least one adhesive particle has a mean length greater than 1 micron, such as from about 5 to about 1000 microns and such as from about 10 to about 100 microns. The mean length of the at least one adhesive particle may be measured by the following methods: optical microscopy, sieving, sedimentation, radiant diffusion, absorption, Coulter's principle, laser light ndiffraction, X-ray, and Sensing-zone method, which are described by Clyde Orr, "Size Measurement of Particles," in *Kirk-Othmer Encyclopedia of Chemical Technology*, vol. 21, pp. 106–131 ($3^{rd}$ ed. 1983) and by Terry Allen, "Analyse et Caractérisation, Technique de l'ingénieur" in Etudes de Structure-Granulométrie, vol.12, pp.1040–9 to 1040–26 (1996). In one embodiment, optical microscopy is used to determine the mean length of the at least one adhesive particle.

In one embodiment, the at least one adhesive particle useful in the practice of the invention may be chosen by measuring the maximum tensile force, $F_{max}$, required while separating two surfaces. An adhesive particle with an $F_{max}$ that is effective for holding and/or reshaping hair may be useful in the practice of the invention. Depending on the application envisaged and the formulation being designed, the desirable value for $F_{max}$ may vary. In some embodiments, adhesive particles with an $F_{max}$ of greater than about 0.5 Newton (N), greater than about 1 N, or greater than about 4 N may be useful in the practice of the invention. One of ordinary skill in the art can determine the $F_{max}$ of the at least one adhesive particle by, for example, determining the maximum force of traction, measured with an extensiometer of the LLOYD model LR5K type, needed to detach two surfaces.

In one embodiment, two 38 $mm^2$ surfaces, A and B, which are solid, rigid, inert, and non-absorbing, are mounted on movable mounts, facing each other. The surfaces may be movable either toward or away from each other, or one may move surface A independently from surface B or vice versa. Prior to insertion into the extensiometer, surface A is coated with the at least one adhesive particle previously dispersed at a concentration of 10% in a solvent chosen from aqueous, hydroalcoholic, and alcoholic solvents at a level of 1 $mg/mm^2$. The level surface is dried for 24 hours at 22° C. at a relative humidity of 50%. Once inserted in the extensiometer, surface A is subjected for 20 seconds to a compression force of 3 N against surface B and then subjected for 30 seconds to tensile force at a rate of 20 mm/minute. The amount of force, $F_{max}$, needed to obtain initial separation is then noted. A mean $F_{max}$ is determined by carrying out the procedure with six pairs of surface A and surface B.

In another embodiment, the at least one adhesive particle useful in the practice of the invention may be chosen based on the energy of separation, $E_s$, the energy supplied by the extensiometer to separate two surfaces. One of skill in the art may determine the $E_s$ of the at least one adhesive particle using the LLOYD model LR5K type extensiometer and other experimental procedure described in the preceding paragraphs.

In one embodiment, two 38 $mm^2$ surfaces, C and D, which are solid, rigid, inert, and non-absorbing, are mounted on movable mounts, facing each other. Only surface C is coated, as above, with the at least one adhesive particle dispersed in a solvent. The $E_s$ is measured with the LLOYD extensiometer and may be calculated from the following formula:

$$\int_{X_{s1}+0.05}^{X_{s2}} F(x)\,dx \qquad (I)$$

where F(x) is the force required to produce a displacement (x); $X_{s1}$ is the displacement, expressed in millimeters, produced at the maximum tensile force; and $X_{s2}$ is the displacement, expressed in millimeters, produced by the tensile force, which permits the total separation of the two surfaces, C and D.

In one embodiment, the at least one adhesive particle useful in the practice of the invention has an $E_s$ of less than 300 μJ when placed in contact with a glass surface. For example, the adhesives of WO 98/38969, the disclosure of which related to such adhesives is incorporated herein by reference, in particular the anionic and nonionic adhesives, may be useful in the manufacture of the at least one adhesive particle.

The adhesives that may be useful in formulating the at least one adhesive of the at least partial coating and/or the at least one substrate of the invention are not limited to polymeric adhesives. Useful adhesives may be nonsoluble in the optional cosmetically acceptable carrier. In particular, by "adhesive" is meant that when applied as a solution to a surface, e.g., the hair or skin, and dried the adhesive forms films or welds. Such a film or weld will have adhesive and cohesive strength, as is understood by those skilled in the art. Useful examples include the adhesives of WO 98/48770, the disclosure of which related to such adhesives is incorporated herein by reference.

In one embodiment, the adhesive that may be useful in formulating the at least one adhesive of the at least partial coating and/or the at least one substrate of the invention is chosen from polymeric adhesives, for example fixing polymers, such as anionic, cationic, amphoteric (such as zwitterionic), and nonionic fixing polymers and combinations thereof. As used herein, the term "polymer" refers to homopolymers and copolymers, the copolymers being derived from more than one type of monomer, such as from two, three, four, or more different monomer types.

The cationic fixing polymers comprise cationic moieties or moieties that are convertible to cationic moieties. Suitable examples of cationic fixing polymers, which can be used according to the present invention, are those that may be chosen from polymers comprising at least one group chosen from primary amine groups, secondary amine groups, tertiary amine groups, and quaternary amine groups, wherein the at least one group forms part of the polymer chain or is linked directly to it, having a weight average molecular weight ranging from about 500 to about 5,000,000, such as from about 100 to about 3,000,000.

Among these polymers, mention may be made more particularly of the following cationic fixing polymers:

(1) homopolymers and copolymers derived from monomers chosen from (meth)acrylic esters and (meth)acrylic amides comprising units of at least one of the following formulae:

(A)
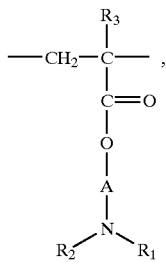

(B)
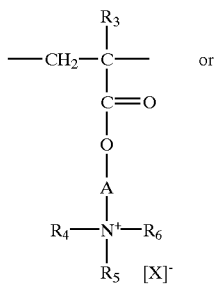
or (C)
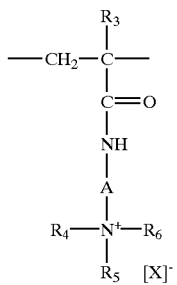

in which each $R_3$ is independently chosen from hydrogen and $CH_3$ groups; each A is independently chosen from linear and branched alkyl groups comprising 1 to 6 carbon atoms and hydroxyalkyl groups comprising 1 to 4 carbon atoms; each $R_4$, $R_5$, and $R_6$ is independently chosen from alkyl groups comprising 1 to 18 carbon atoms and benzyl groups; each $R_1$ and $R_2$ is independently chosen from hydrogen and alkyl groups comprising 1 to 6 carbon atoms; and each $X^-$ is independently chosen from methyl sulfate anions and halide anions, such as chloride or bromide anions.

In one embodiment, the copolymers of family (1) further comprise at least one unit derived from monomers chosen from (meth)acrylamides, diacetone (meth)acrylamides, (meth)acrylamides substituted on the nitrogen by a group chosen from lower alkyls, (meth)acrylic acids, esters of (meth)acrylic acids, vinyllactams such as vinylpyrrolidone and vinyl-caprolactam, and vinyl esters.

Thus, mention may be made, among these cationic copolymers of the family (1), of:

copolymers of acrylamide and of dimethylaminoethyl methacrylate quaternized with dimethyl sulfate or with a dimethyl halide, such as that sold under the name Hercofloc by the company Hercules;

copolymers of acrylamide and of methacryloyloxyethyl-trimethylammonium chloride which are disclosed, for example, in EP-A-080,976, the disclosure of which relating to cationic polymers is incorporated herein by reference, and sold, for example, under the name Bina Quat P 100 by the company Ciba-Geigy;

copolymers of acrylamide and of methacryloyloxyethyl-trimethylammonium methosulfate, such as that sold under the name Reten by the company Hercules;

optionally quaternized vinylpyrrolidone/dialkyl-aminoalkyl (meth)acrylate copolymers, which are disclosed, for example, in French Patents 2,077,143 and 2,393,573, the disclosures of which relating to cationic polymers are incorporated herein by reference, and sold, for example, under the name "Gafquat" by the company ISP, such as, for example, "Gafquat 734" or "Gafquat 755", or else the products named "Copolymer 845, 958 and 937";

dimethylaminoethyl methacrylate/vinylcaprolactam/vinylpyrrolidone terpolymers, such as the product sold under the name Gaffix VC 713 by the company ISP, and the quaternized vinylpyrrolidone/dimethylamino-propylmethacrylamide copolymer, such as the product sold under the name "Gafquat HS 100" by the company ISP;

(2) the quaternized polysaccharides, disclosed more particularly in U.S. Pat. Nos. 3,589,578 and 4,031,307, the disclosures of which relating to quaternized polysaccharides polymers are incorporated herein by reference, such as guar gums comprising cationic trialkylammonium cationic groups.

Such products are sold in particular under the trade names Jaguar C 13 S, Jaguar C 15, and Jaguar C 17 by the company Meyhall.

(3) quaternized copolymers of vinylpyrrolidone and of vinylimidazole, such as the products sold by BASF under the name Luviquat TFC.

(4) chitosans or their salts. The salts, which can be used, are in particular chitosan acetate, lactate, glutamate, gluconate, or pyrrolidone-carboxylate.

Mention may be made, among these compounds, of the chitosan having a degree of deacetylation of 90.5% by weight sold under the name Kytan Crude Standard by the company Aber Technologies and the chitosan pyrrolidone-carboxylate sold under the name Kytamer PC by the company Amerchol.

(5) Cationic cellulose derivatives, such as the copolymers of cellulose and the cellulose derivatives grafted with a water-soluble quaternary ammonium monomer and disclosed in particular in U.S. Pat. No. 4,131,576, the disclosure of which relating to cationic cellulose derivatives is incorporated herein by reference. Examples include hydroxyalkyl celluloses, for example hydroxymethyl, hydroxyethyl, and hydroxypropyl celluloses grafted in particular with a methacryloylethyltrimethylammonium, methacrylamidopropyltrimethylammonium, or diallyldimethylammonium salt.

The commercial products corresponding to this definition are more particularly the products sold under the name "Celquat L 200" and "Celquat H 100" by the company National Starch.

The anionic fixing polymers, which can be used according to the present invention, are polymers comprising groups derived from carboxylic, sulfonic, and/or phosphoric acid and having a weight average molecular weight ranging from about 500 to about 5,000,000.

(1) The carboxyl groups may be contributed by unsaturated mono- or dicarboxylic acid monomers such as those corresponding to the formula:

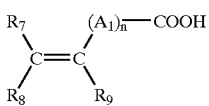

(II)

in which n is an integer ranging from 0 to 10; $A_1$ denotes a methylene group and when n is greater than 1, each $A_1$ is independently represented by —$LCH_2$—, where L is chosen from a valency bond and heteroatoms, such as oxygen and sulfur; $R_7$ is chosen from hydrogen, phenyl groups, and benzyl groups; $R_8$ is chosen from hydrogen, lower alkyl groups, and carboxyl groups; and $R_9$ is chosen from hydrogen, lower alkyl groups, —$CH_2$—COOH groups, phenyl groups, and benzyl groups.

As defined herein, a lower alkyl group denotes a group having 1 to 4 carbon atoms, such as methyl and ethyl.

The anionic fixing polymers comprising carboxyl groups according to the invention may be chosen from:

A) Homopolymers and copolymers of (meth)acrylic acids or (meth)acrylic salts and in particular the products sold under the names Versicol E or K by the company Allied Colloid and Ultrahold by the company BASF, the copolymers of acrylic acid and of acrylamide sold in the form of their sodium salt under the names Reten 421, 423, or 425 by the company Hercules, and the sodium salts of polyhydroxycarboxylic acids.

B) Copolymers of (meth)acrylic acid with a monoethylenic monomer, such as ethylene, styrene, vinyl esters, and (meth)acrylic acid esters, optionally grafted onto a polyalkylene glycol, such as polyethylene glycol, and optionally crosslinked. Such polymers are disclosed in particular in French Patent 1,222,944 and German Application 2,330,956, the disclosures of which relating to such copolymers are incorporated herein by reference. The copolymers of this type comprising, in their chain, an optionally N-alkylated and/or hydroxyalkylated acrylamide unit, such as disclosed in particular in Luxembourg Patent Applications 75370 and 75371, the disclosures of which relating to such copolymers are incorporated herein by reference, or sold under the name Quadramer by the company American Cyanamid. Mention may also be made of copolymers of acrylic acid and of $C_1$–$C_4$ alkyl methacrylate and terpolymers of vinylpyrrolidone, of acrylic acid, and of $C_1$–$C_{20}$ alkyl methacrylate for example lauryl methacrylate, such as that sold by the company ISP under the name Acrylidone LM, and methacrylic acid/ethyl acrylate/tert-butyl acrylate terpolymers, such as the product sold under the name Luvimer 100 P by the company BASF.

C) copolymers derived from crotonic acid, such as those comprising, in their chain, vinyl acetate or propionate units and optionally other monomers, such as (meth)allyl esters, vinyl ether or vinyl ester of a linear or branched saturated carboxylic acid comprising a long hydrocarbon chain, such as those comprising at least 5 carbon atoms, it optionally being possible for these polymers to be grafted and crosslinked, or alternatively a vinyl, allyl, or methallyl ester of an α- or β-cyclic carboxylic acid. Such polymers are disclosed, inter alia, in French Patents 1,222,944, 1,580,545, 2,265,782, 2,265,781, 1,564,110, and 2,439,798, the disclosures of which relating to copolymers of crotonic acid are incorporated herein by reference. Commercial products coming within this class are the Resins 28-29-30, 26-13-14, and 28-13-10 sold by the company National Starch.

D) copolymers derived from $C_4$–$C_8$ monounsaturated carboxylic acids or anhydrides chosen from:

copolymers comprising units derived from (i) at least one monomer chosen from maleic, fumaric, and itaconic acids and anhydrides thereof and (ii) at least one monomer chosen from vinyl esters, vinyl ethers, vinyl halides, phenylvinyl derivatives, acrylic acids, and acrylic acid esters, the anhydride functional groups of these copolymers optionally being monoesterified or monoamidated. Such polymers are disclosed in particular in U.S. Pat. Nos. 2,047,398, 2,723,248, and 2,102,112 and GB 839,805, the disclosures of which relating to such copolymers are incorporated herein by reference, and in particular those sold under the names Gantrez AN or ES by the company ISP.

copolymers comprising units derived from (i) at least one monomer chosen from maleic, citraconic, and itaconic anhydrides and (ii) at least one monomer chosen from (meth)allyl esters, optionally comprising in their chain at least one unit derived from groups chosen from (meth)acrylamide, α-olefin, (meth)acrylic ester, (meth)acrylic acid, and vinylpyrrolidone groups. The anhydride functional groups of these copolymers optionally are monoesterified or monoamidated.

These polymers are, for example, disclosed in French Patents 2,350,384 and 2,357,241 the disclosures of which relating to such copolymers are incorporated herein by reference.

E) polyacrylamides comprising carboxylate groups.

(2) The anionic fixing polymers comprising sulfonic groups may be chosen from polymers comprising units, such as those derived from vinylsulfonic, styrenesulfonic, naphthalenesulfonic, and acrylamidoalkylsulfonic acids and their derivatives. These polymers may be chosen from:

salts of polyvinylsulfonic acid having a weight average molecular weight that ranges from about 1000 to about 100,000, as well as the copolymers derived from at least one unsaturated comonomer, such as acrylic and methacrylic acids, their esters, acrylamides, their derivatives, vinyl ethers, and vinylpyrrolidone;

salts of polystyrenesulfonic acid, the sodium salts having a weight average molecular weight ranging from about 100,000 to about 500,000, which are sold respectively under the names Flexan 500 and Flexan 130 by National Starch. These compounds are disclosed in Patent FR 2,198,719, the disclosure of which relating to salts of polystyrenesulfonic acid is incorporated herein by reference;

salts of polyacrylamidesulfonic acids, including those mentioned in U.S. Pat. No. 4,128,631, the disclosure of which relating to salts of polyacrylamidesulfonic acid is incorporated herein by reference, and more particularly the polyacrylamidoethylpropanesulfonic acid sold under the name Cosmedia Polymer HSP 1180 by Henkel.

In one embodiment, the anionic fixing polymers are chosen from acrylic acid copolymers, such as the acrylic acid/ethyl acrylate/N-tert-butylacrylamide terpolymer sold under the name Ultrahold Strong by the company BASF; copolymers derived from crotonic acid, such as the vinyl acetate/vinyl tert-butyl-benzoate/crotonic acid terpolymers and the crotonic acid/vinyl acetate/vinyl neododecanoate terpolymers sold under the name Resin 28-29-30 by the company National Starch; polymers derived from at least one monomer chosen from maleic, fumaric, and itaconic acids and anhydrides thereof and also from at least one monomer chosen from vinyl esters, vinyl ethers, vinyl halides, phenylvinyl derivatives, acrylic acid, and esters of acrylic acid, such as the monoesterified methyl vinyl ether/ maleic anhydride copolymer sold under the name Gantrez ES 425 by the company ISP; copolymers of methacrylic acid and of methyl methacrylate sold under the name Eudragit L by the company Rohm Pharma; the copolymer of methacrylic acid and of ethyl acrylate sold under the name Luvimer MAEX or MAE by the company BASF; the vinyl acetate/crotonic acid copolymer sold under the name Luviset CA 66 by the company BASF; and the vinyl acetate/crotonic acid copolymer grafted by polyethylene glycol sold under the name Aristoflex A by the company BASF.

In another embodiment, the anionic fixing polymers are chosen from the monoesterified methyl vinyl ether/maleic anhydride copolymer sold under the name Gantrez ES 425 by the company ISP; the acrylic acid/ethyl acrylate/N-tert-butylacrylamide terpolymer sold under the name Ultrahold Strong by the company BASF; the copolymers of methamrylic acid and of methyl methacrylate sold under the name Eudragit L by the company Rohm Pharma; the vinyl acetate/ vinyl tert-butylbenzoate/crotonic acid terpolymers and the crotonic acid/vinyl acetate/vinyl neododecanoate terpolymers sold under the name Resin 28-29-30 by the company National Starch; the copolymer of methacrylic acid and of ethyl acrylate sold under the name Luvimer MAEX or MAE by the company BASF; and the vinyl-pyrrolidone/acrylic acid/lauryl methacrylate terpolymer sold under the name Acrylidone LM by the company ISP.

The amphoteric fixing polymers, which can be used in accordance with the invention, may be chosen from polymers comprising X and Y units, distributed randomly in the polymer chain, where the X unit is chosen from units derived from at least one monomer comprising at least one basic function, in particular a basic nitrogen atom, and where the Y unit is chosen from units derived from at least one acidic monomer comprising at least one group chosen from carboxyl groups and sulfo groups, or else where each X and Y unit is independently chosen from groups derived from zwitterionic carboxybetaine and sulfobetaine monomers. In another embodiment, the amphoteric fixing polymers, which can be used in accordance with the invention, may be chosen from polymers comprising X and Y units, each X and Y unit is independently chosen from at least one cationic polymer chain comprising at least one group chosen from primary amine groups, secondary amine groups, tertiary amine groups, and quaternary amine groups, in which at least one of the amine groups comprises a group chosen from carboxyl and sulfo groups linked by way of a hydrocarbon group, or else the X and Y units, which may be different or identical, form part of a chain of at least one polymer comprising an α,β-dicarboxy ethylene unit, wherein at least one of the carboxyl groups has been reacted with a polyamine comprising at least one group chosen from primary and secondary amine groups.

In one embodiment, the amphoteric fixing polymers corresponding to the definition given above are chosen from the following polymers:

(1) polymers resulting from the copolymerization of a monomer derived from a vinyl compound carrying a carboxyl group, such as (meth)acrylic acids, maleic acids, and α-chloracrylic acids, and of a basic monomer derived from a substituted vinyl compound comprising at least one basic atom, such as dialkylaminoalkyl (meth)acrylate and dialkylaminoalkyl (meth) acrylamide. Such compounds are disclosed in U.S. Pat. No. 3,836,537, the disclosure of which relating to amphoteric polymers is incorporated herein by reference.

(2) polymers comprising units derived from:
 a) at least one monomer chosen from (meth) acrylamides substituted on the nitrogen with an alkyl group,
 b) at least one acidic comonomer comprising at least one reactive carboxylic group, and
 c) at least one basic comonomer, such as esters comprising at least one substituent chosen from primary, secondary, tertiary, and quaternary amine substituents of (meth)acrylic acids, and the product of quaternization of dimethylaminoethyl methacrylate with dimethyl or diethyl sulfate.

The at least one N-substituted (meth)acrylamide monomer recited in (a) is more particularly chosen from N-substituted (meth)acrylamides, wherein the alkyl groups comprise from 2 to 12 carbon atoms, such as N-ethylacrylamide, N-tert-butylacrylamide, N-tert-octylacrylamide, N-octylacrylamide, N-decylacrylamide, N-dodecylacrylamide, and the corresponding methacrylamides.

The at least one acidic comonomer recited in (b) is more particularly chosen from (meth)acrylic acids, crotonic acids, itaconic acids, maleic acids, fumaric acids, $C_1$–$C_4$ alkyl monoesters of maleic acid, $C_1$–$C_4$ alkyl monoesters of fumaric acid, $C_1$–$C_4$ alkyl monoesters of maleic anhydride, and $C_1$–$C_4$ alkyl monoesters of fumaric anhydride.

The at least one basic comonomer recited in (c) is more particularly chosen from aminoethyl, butylaminoethyl, N,N'-dimethylaminoethyl, and N-tert-butylaminoethyl methacrylates.

In one embodiment, the amphoteric fixing polymer is chosen from the copolymers for which the CTFA name (4th Ed., 1991) is octylacrylamide/acrylates/butylaminoethyl methacrylate copolymer, such as the products sold under the name Amphomer or Lovocryl 47 by the company National Starch.

(3) crosslinked and alkylated polyamino amides partially or totally derived from polyamino amides of general formula:

in which $R_{10}$ represents a divalent group derived either from a saturated dicarboxylic acid, from an aliphatic mono- or dicarboxylic acid comprising an ethylenic double bond, from an ester of a lower alkanol having 1 to 6 carbon atoms of these acids, or from a group derived from the addition of any one of the said acids with a bisprimary or bissecondary amine; and Z denotes a group of a bisprimary, mono- or bissecondary polyalkylenepolyamine and, for example, represents:

a) in the proportions of from about 60 mol % to 100 mol %, the group:

where x=2 and p=2 or 3, or else x=3 and p=2 and where this group derives from diethylenetriamine, triethylenetetraamine, or dipropylenetriamine;

b) in the proportions of from 0 mol % to about 40 mol %, the above group (IV), in which x=2 and p=1 and which derives from ethylenediamine, or the group derived from piperazine:

c) in the proportions of from 0 mol % to about 20 mol %, the —NH—(CH$_2$)$_6$—NH— group derived from hexamethylenediamine, these polyamino amines being crosslinked by addition of a difunctional crosslinking agent chosen from epihalohydrines, diepoxides, dianhydrides and bis-unsaturated derivatives, using from about 0.025 mol to about 0.35 mol of crosslinking agent per amine group of the polyamino amide and alkylated by the action of acrylic acid, chloroacetic acid or an alkane sultone, or salts thereof.

In one embodiment, the saturated carboxylic acids are chosen from acids having 6 to 10 carbon atoms, such as adipic acid, 2,2,4-trimethyladipic acid, 2,4,4-trimethyladipic acid, terephthalic acid, and acids comprising an ethylenic double bond such as, for example, acrylic acid, methacrylic acid and itaconic acid.

In one embodiment, the alkane sultones used in the alkylation are chosen from propane sultone and butane sultone and the salts of the alkylating agents are chosen from sodium and potassium salts.

(4) polymers comprising zwitterionic units of formula:

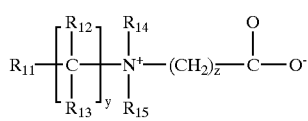

(V)

in which $R_{11}$ is chosen from polymerizable unsaturated groups such as a (meth)acrylate and (meth)acrylamide groups; y and z are independently chosen from integers ranging from 1 to 3; $R_{12}$ and $R_{13}$ are independently chosen from hydrogen, methyl groups, ethyl groups, and propyl groups; $R_{14}$ and $R_{15}$ are independently chosen from hydrogen and alkyl groups, wherein the sum of the carbon atoms in $R_{14}$ and $R_{15}$ is less than or equal to 10.

The polymers comprising such units may further comprise units derived from non-zwitterionic monomers, such as dimethylaminoethyl (meth)acrylate, diethylaminoethyl (meth)acrylate, alkyl (meth)acrylates, (meth)acrylamides, and vinyl acetates.

Mention may be made, by way of example, of the methyl methacrylate/ methyl dimethylcarboxymethylammonioethyl methacrylate copolymer, such as the product sold under the name Diaformer Z301 by the company Sandoz.

(5) polymers derived from chitosan comprising monomer units corresponding to the following formulae:

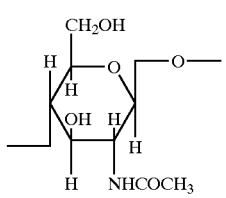

(D)

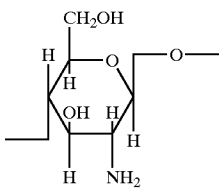

(E)

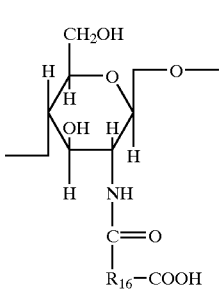

(F)

the unit D being present in proportions ranging from 0% to about 30%, the unit E in proportions ranging from about 5% to about 50% and the unit F in proportions ranging from about 30% to about 90%, it being understood that, in this unit F, $R_{16}$ represents a group of formula:

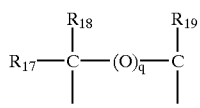

in which, if q=0, $R_{17}$, $R_{18}$, and $R_{19}$, which are identical or different, are chosen from hydrogen, methyl groups, hydroxyl groups, acetoxy groups, amino residues, monoalkylamine residues, and dialkylamine residues, optionally interrupted by one or more nitrogen atoms and/or optionally substituted by one or more amine, hydroxyl, carboxy, alkylthio, or sulfo groups, and alkylthio residues in which the alkyl group carries an amino residue, at least one of $R_{17}$, $R_{18}$, and $R_{19}$ being, in this case, hydrogen; or, if q=1, $R_{17}$, $R_{18}$, and $R_{19}$ each represent hydrogen, and the salts formed by these compounds with bases or acids.

(6) Polymers derived from the N-carboxyalkylation of chitosan, such as the N-(carboxymethyl)chitosan or the N-(carboxybutyl)chitosan sold under the name "Evalsan" by the company Jan Dekker.

(7) Polymers corresponding to the general formula (VI), for example disclosed in French Patent 1,400,366, the disclosure of which relating to amphoteric polymers is incorporated herein by reference:

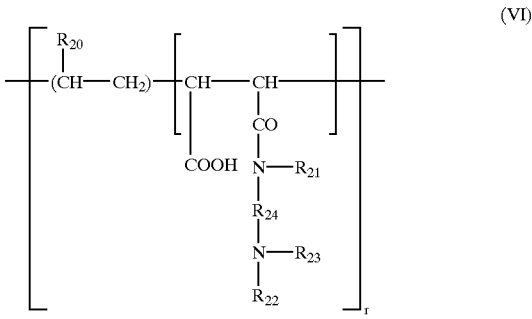

(VI)

in which $R_{20}$ is chosen from hydrogen, $CH_3O$, $CH_3CH_2O$, and phenyl groups; $R_{21}$ is chosen from hydrogen and lower alkyl groups such as methyl or ethyl; $R_{22}$ is chosen from hydrogen and lower alkyl groups such as methyl or ethyl; and $R_{23}$ is chosen from lower alkyl groups such as methyl or ethyl and groups corresponding to the formula: $-R_{24}-N(R_{22})_2$, where $R_{24}$ is chosen from $-CH_2-CH_2-$, $-CH_2-CH_2-CH_2-$, and $-CH_2-CH(CH_3)-$ groups and $R_{22}$ is the same as above, and the higher homologues of these groups comprising up to 6 carbon atoms.

(8) Amphoteric fixing polymers of the $-D-X-D-X-$ type chosen from:

a) polymers obtained by reaction of chloracetic acid or sodium chloracetate with compounds comprising at least one unit of formula:

$$-D-X-D-X-D- \quad (VII)$$

where D denotes a group

and X denotes the symbol E or E', E and E', which are identical or different, denote a divalent group chosen from straight- and branched-chain alkylene groups comprising up to 7 carbon atoms in the main chain, which is unsubstituted or substituted by hydroxyl groups and which can additionally comprise oxygen, nitrogen, or sulfur atoms or 1 to 3 aromatic and/or heterocyclic rings; the oxygen, nitrogen, and sulfur atoms being present in the form of ether, thioether, sulfoxide, sulfone, sulfonium, alkylamine or alkenylamine groups, benzylamine, amine oxide, quaternary ammonium, amide, imide, alcohol, ester, and/or urethane groups.

b) Polymers of formula:

$$-D-X-D-X- \quad (VII')$$

in which D denotes a group

and X denotes the symbol E or E' and E' at least once, where E has the meaning indicated above and E' is a divalent group chosen from straight- and branched-chain alkylene groups having up to 7 carbon atoms in the main chain, which is substituted or unsubstituted by one or more hydroxyl groups and which comprises one or more nitrogen atoms, the nitrogen atom being substituted by an alkyl chain optionally interrupted by an oxygen atom and necessarily comprising one or more carboxyl functional groups or one or more hydroxyl functional groups and wherein the polymer of formula VII' is betainized by reaction with chloracetic acid or sodium chloracetate.

(9) $(C_1-C_5)$alkyl vinyl ether/maleic anhydride copolymers, which are partially modified by semiamidation with an N,N-dialkylaminoalkylamine, such as N,N-dimethylaminopropylamine, or by semiesterification with an N,N-dialkanolamine. These copolymers can also comprise other vinyl comonomers, such as vinylcaprolactam.

In one embodiment, the amphoteric fixing polymers according to the invention are chosen from family (3), such as the copolymers with the CTFA name ($4^{th}$ Ed. 1991) of octylacrylamide/acrylates/butylaminoethyl methacrylate copolymer, such as the products sold under the names Amphomer, Amphomer LV 71, or Lovocryl 47 by the company National Starch, and family (4), such as the copolymer of methyl methacrylate/dimethyl carboxymethylammonio methyl ethylmethacrylate, sold, for example, under the name Diaformer Z301 by the company Sandoz.

The nonionic fixing polymers, which can be used according to the present invention, are chosen, for example, from:

vinylpyrrolidone homopolymers;

copolymers of vinylpyrrolidone and of vinyl acetate;

polyalkyloxazolines, such as the polyethyloxazolines sold by the company Dow Chemical under the names PEOX 50 000, PEOX 200 000 and PEOX 500 000;

vinyl acetate homopolymers, such as the product sold under the name Appretan EM by the company Hoechst or the product sold under the name Rhodopas A 012 by the company Rhône-Poulenc;

copolymers of vinyl acetate and of acrylic ester, such as the product sold under the name Rhodopas AD 310 by Rhône-Poulenc;

copolymers of vinyl acetate and of ethylene, such as the product sold under the name Appretan TV by the company Hoechst;

copolymers of vinyl acetate and of maleic ester, for example of dibutyl maleate, such as the product sold under the name Appretan MB Extra by the company Hoechst;

copolymers of polyethylene and of maleic anhydride;

alkyl acrylate homopolymers and alkyl methacrylate homopolymers, such as the product sold under the name Micropearl RQ 750 by the company Matsumoto or the product sold under the name Luhydran A 848 S by the company BASF;

acrylic ester copolymers such as, for example, copolymers of alkyl (meth)acrylates, such as the products sold by the company Rohm & Haas under the names Primal AC-261 K and Eudragit NE 30 D, by the company BASF under the names Acronal 601, Luhydran LR 8833 or 8845, and by the company Hoechst under the names Appretan N 9213 or N 9212;

copolymers of acrylonitrile and of a nonionic monomer chosen, for example, from butadiene and alkyl (meth) acrylates; mention may be made of the products sold under the names Nipol LX 531 B by the company Nippon Zeon or those sold under the name CJ 0601 B by the company Rohm & Haas;

polyurethanes, such as the products sold under the names Acrysol RM 1020 or Acrysol RM 2020 by the company Rohm & Haas, and the products Uraflex XP 401 UZ and Uraflex XP 402 UZ by the company DSM Resins;

copolymers of alkyl acrylate and of urethane, such as the product 8538-33 by the company National Starch;

polyamides, such as the product Estapor LO 11 sold by the company Rhône-Poulenc.

nonionic guar gums that are chemically modified or unmodified.

The unmodified nonionic guar gums are, for example, the products sold under the name Vidogum GH 175 by the company Unipectine and under the name Jaguar C by the company Meyhall.

The modified nonionic guar gums, which may be used according to the invention, are, for example, modified with $C_1$–$C_6$ hydroxyalkyl groups. Examples, which may be mentioned, are hydroxymethyl, hydroxyethyl, hydroxypropyl, and hydroxybutyl groups.

These guar gums are well known in the prior art and may be prepared, for example, by reacting corresponding alkene oxides such as, for example, propylene oxides with guar gum so as to obtain a guar gum modified with hydroxypropyl groups.

Such nonionic guar gums, optionally modified with hydroxyalkyl groups, are sold, for example, under the trade names Jaguar HP8, Jaguar HP60, Jaguar HP120, Jaguar DC 293 and Jaguar HP 105 by the company Meyhall and under the name Galactosol 4H4FD2 by the company Aqualon.

The alkyl groups in the nonionic polymers comprise from I to 6 carbon atoms, except where otherwise mentioned.

According to the invention, it is also possible to use fixing polymers of grafted silicone type comprising a polysiloxane portion and a portion comprising a non-silicone organic chain, one of the two portions constituting the main chain of the polymer and the other being grafted onto the said main chain. These polymers are disclosed, for example, in EP-A-0,412,704, EP-A-0,412,707, EP-A-0,640,105, WO 95/00578, EP-A-0,582,152, and WO 93/23009 and U.S. Pat. Nos. 4,693,935, 4,728,571, and 4,972,037, the disclosures of which relating to grafted silicone type polymers are incorporated herein by reference. These polymers are, for example, anionic or nonionic.

Such polymers are, for example, copolymers which can be obtained by radical polymerization from the monomer mixture comprising:
a) about 50% to about 90% by weight of tert-butyl acrylate;
b) 0% to about 40% by weight of acrylic acid;
c) about 5% to about 40% by weight of silicone macromer of formula:

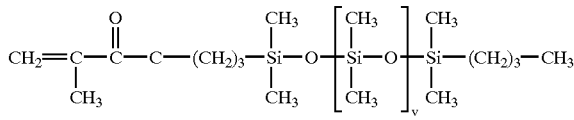

where v is a number ranging from 5 to 700; the percentages by weight being calculated with respect to the total weight of the monomers.

Other examples of grafted silicone polymers are, in particular, polydimethylsiloxanes (PDMSs) onto which are grafted, via a thiopropylene-type connecting chain, mixed polymer units of the poly(meth)acrylic acid type and of the poly(alkyl (meth)acrylate) type and polydimethylsiloxanes (PDMSs) onto which are grafted, via a thiopropylene-type connecting chain, polymer units of the poly(isobutyl (meth) acrylate) type.

It is also possible to use, as fixing polymers, functionalized or non-functionalized and silicone-comprising or non-silicone-comprising polyurethanes.

Examples of useful polyurethanes include those disclosed in Patents EP 0,751,162, EP 0,637,600, FR 2,743,297, EP 0,648,485, EP 0,656,021, WO 94/03510, and EP 0,619,111, the disclosure of which relating to polyurethanes are incorporated herein by reference.

In a further embodiment, the fixing polymers may be used in solubilized form or may be in the form of dispersions of solid particles (latex or pseudo-latex).

In another embodiment, the at least one adhesive of the at least partial coating and/or the at least one substrate of the invention may be chosen from polymeric adhesives, such as (meth)acrylic copolymers comprising: (a) units derived from at least one monomer present at from about 0.1 to about 99% by weight, such as about 9 to about 99% by weight of the total weight of the polymer and (b) units derived from at least one co-monomer present at up to about 99.9% by weight, such as up to about 91% by weight.

The at least one monomer recited in (a) can generally be represented by formula:

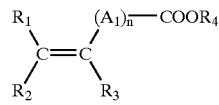

in which n is an integer ranging from 0 to 10; $A_1$ denotes a methylene group and when n is greater than 1, each $A_1$ is independently represented by —$LCH_2$—, where L is chosen from a valency bond and heteroatoms, such as oxygen and sulfur; $R_1$ is chosen from hydrogen, phenyl groups, and benzyl groups; $R_2$ is chosen from hydrogen, lower alkyl groups, and carboxyl groups; and $R_3$ is chosen from hydrogen, lower alkyl groups, —$CH_2$—COOH groups, phenyl groups, and benzyl groups; and $R_4$ is chosen from hydrogen, $C_1$ to $C_{18}$ alkyls, $C_2$ to $C_8$ alkoxyalkyls, $C_2$ to $C_8$ alkylthioalkyls, and $C_2$ to $C_8$ cyanoalkyls.

The at least one monomer recited in (a) may, for example, be chosen from acrylic acids, methacrylic acids, salts thereof, and derivatives thereof, such as acrylic and methacrylic esters, including methyl acrylate, ethyl acrylate, n-butyl acrylate, isobutyl acrylate, hexyl acrylate, octyl acrylate, 2-ethylhexyl acrylate, decyl acrylate, methoxyacrylate, ethoxyacrylate, methylthiomethyl acrylate, and cyanopropyl acrylate.

The at least one co-monomer recited in (b) may contain one or more terminal $CH_2$=C groups, for instance, acrylic or methacrylic esters such as methyl methacrylate, ethyl methacrylate, n-butyl methacrylate, and methyl methacrylate; vinyl halides such as vinyl chlorides; vinyl or allyl esters such as vinyl acetate, vinyl butyrate, and vinyl chloroacetate; and aromatic vinyls such as styrene, vinyltoluene, chloromethylstyrene, and vinyinaphthalene.

In a further embodiment, these (meth)acrylic copolymers may further comprise (c) units derived from at least one vinylidene co-monomer containing at least one group chosen from carboxyl and hydroxyl groups present at from about 1 to about 10% by weight.

Among the at least one vinylidene co-monomer recited in (c) containing at least one hydroxyl group, one may use, for example, acrylate monomers with a terminal hydroxyl group, such as hydroxyethyl acrylate, hydroxyethyl methacrylate, hydroxypropyl acrylate or some other hydroxymethylated diacetone acrylamide derivatives such as N-methylol acrylamide, N-methylol maleamide, N-propanolacrylamide, N-methylol methacrylamide or N-methylol-p-vinyl benzamide. The at least one vinylidene co-monomer recited in (c) containing at least one carboxyl group may be chosen from, for instance, acrylic acid, methacrylic acid, itaconic acid, citraconic acid, crotonic acid, and maleic acid.

Examples of adhesive particles useful in the practice of the invention include the Gel-Tac 100 A, 100 B, 100 C, and 100K Microspheres (API Company), which have a diameter (mean length) of 35 microns, 45 microns, 25 microns, and 10 microns, respectively. The Gel-Tac Microspheres comprise a substrate coated with an acrylic polymer. Other adhesives that may be useful in manufacture of hair styling compositions include the polymers described in WO 98/53794, WO 98/48772, WO 98/48771, WO 97/15725, WO 99/00105, WO 93/23446, WO 96/32920, WO 98/51276, and WO 98/49213, and U.S. Pat. Nos. 5,019,377, 4,963,348, and 5,565,193, the disclosures of which related to adhesives are incorporated herein by reference.

In yet another embodiment of the invention, the adhesive that may be useful in formulating the at least one adhesive of the at least partial coating and/or the at least one substrate of the invention has a glass transition temperature (Tg) ranging from about −100° C. to about 15° C. The Tg of the adhesive is obtained following the application of the adhesive to a substrate and drying. The glass transition temperature is determined by the Differential Scanning Calorimetric method (DSC).

The at least one adhesive particle may be formulated in a composition comprising any cosmetically acceptable carrier that does not substantially interfere with the adhesive and/or reshapable properties of the at least one adhesive particle. In one embodiment, the at least one adhesive particle is insoluble in the cosmetically acceptable carrier. In another embodiment, the at least one adhesive particle is present in a reshapable hair styling composition at a concentration ranging from about 0.1% to about 50% relative to the total weight of the composition.

One of ordinary skill in the art will choose the appropriate carrier based on the application envisaged. In one embodiment, the compositions of the invention may contain water; an organic solvent such as $C_1$ to $C_4$ alcohols including ethanol or isopropanol, $C_5$ to $C_{10}$ alkanes, acetone, methylethylacetone, methylacetate, ethylacetate, butylacetate, dimethoxyethane, and diethoxyethane; or mixtures thereof, such as a hydroalcoholic mixture. In one embodiment, the carrier may comprise an appropriate solvent to which may be added additives such as gelling agents, foaming agents, and silicones.

The compositions of the present invention may also comprise at least one additive known in the cosmetic arts that does not substantially interfere with the adhesive and/or reshapable properties of the at least one adhesive particle. Such additives may be chosen from, but are not limited to: reducing agents (such as thiols); silanes (such as aminopropyl triethoxy silane); fatty substances; thickeners; antifoaming agents; hydrating agents; fillers; sunscreens (such as UV filters); active haircare agents; perfumes; preservatives; cationic, anionic, nonionic, and amphoteric (such as zwitterionic) surfactants; cationic, anionic, nonionic, and amphoteric (such as zwitterionic) polymers; polyols; proteins; provitamins; vitamins; dyes; tints; bleaches; and pH adjusting agents. Examples of thickeners include cross linked polyacrylic acids, such as Carbopol 980 from BF Goodrich Company. The compositions may also contain a conditioning agent such as, for example, such as silicone fluids, fatty esters, fatty alcohol, long chain hydrocarbons, emollients, lubricants, and penetrants such as lanolin compounds, protein hydrolysates, other protein derivatives, cationic and amphoteric polymers, and cationic surfactants. An example of a cationic silicone conditioning agent is the product DC 939, sold by Dow Corning.

The compositions according to the invention can be provided in any form known from the prior art, which is appropriate for their application to the hair, including in the form of a vaporizable composition such as a spray or aerosol, mousse, gel, stick, mud, or lotion. In one embodiment, a reshapable hair styling composition comprises at least one adhesive particle, as set forth above, wherein said at least one adhesive particle is present in an amount effective to provide a reshapable effect and wherein the hair styling composition is in the form chosen from sprays, aerosols, mousses, gels, sticks, muds, and lotions.

The composition may be in any of the conventional forms of cosmetic composition including, but not limited to, shampoos, conditioners, hair rinses, permanent waving compositions, waving compositions, hair dye compositions, hair straightening compositions, hair fixing products, hair styling gel products, products to be used before or after a hair dye treatment, products to be used before or after a permanent waving treatment, products to be used before or after a hair straightening treatment, and fixing foams.

The composition according to the invention may be vaporizable, for example by a pump or may be a pressurized aerosol composition. It may be vaporizable by a dispensing valve controlled by a dispensing head, which in turn comprises a nozzle, which vaporizes the aerosol composition. A vaporizable composition according to the invention comprises an appropriate solvent. Advantageously, the appropriate solvent comprises at least one solvent chosen from water and lower alcohols. In accordance with the invention, the term "lower alcohol" means a $C_1$ to $C_4$ aliphatic alcohol, such as ethanol.

When the vaporizable composition according to the invention is an aerosol composition, it additionally comprises an appropriate amount of propellant. The propellant comprises compressed or liquefied gases, which are normally employed for the preparation of aerosol compositions. Suitable gases include compressed air, carbon dioxide, nitrogen, and gases, which may be soluble in the composition such as dimethyl ether, fluorinated or non-fluorinated hydrocarbons, and mixtures thereof.

The present invention additionally provides an aerosol device comprising a vessel comprising an aerosol composition, which comprises a liquid phase (or juice) comprising at least one hair styling composition comprising at least one adhesive particle, as described above, in a cosmetically acceptable carrier and a propellant, and a dispenser, such as a dispensing valve, for dispensing the aerosol composition from the vessel. In one embodiment, the at least one adhesive particle is present in an amount effective to provide a reshapable effect.

The present invention also relates to a method of providing styling hold to the hair comprising applying to the hair a hair styling composition that comprises, optionally in a cosmetically acceptable carrier, at least one adhesive particle, as set forth above, wherein the at least one adhesive particle is present in an amount effective to provide a holding effect. In addition, the invention is drawn to a method of providing a reshapable effect to the hair comprising applying to the hair a reshapable hair styling composition that comprises, optionally in a cosmetically acceptable carrier, at least one adhesive particle, as set forth above, wherein the at least one adhesive particle is present in an amount effective to provide a reshapable effect.

Not to be limited as to theory, it is believed that the at least one adhesive particle creates "weld points," as discussed above, between two pieces of hair or among several strands of hair when applied before, during, or after styling. Yet when the at least one adhesive particle imparts a reshapable effect, the passage of a comb, a brush, or even the fingers of one's hand can reshape the hair by breaking these weld points and forming new weld points upon repositioning of the at least one adhesive particle. The hair may be repeatedly reshaped and, thus, the styling may be restored or modified. Each time the hair is styled, the at least one adhesive particle is moved among the hair or the strands of hair and form new weld points in the hair, thus holding the shape. The styling hold is temporary, i.e., the at least one adhesive particle may be used to reshape the hair until removed by washing, or until the adhesive effect is lost by multiple reshaping.

Another aspect of the present invention additionally provides a method of cosmetically treating keratinous fibers, especially hair, comprising applying to the hair before, during, or after the shaping of the hairstyle a hair styling composition comprising at least one adhesive particle, as set forth above. In one embodiment, the at least one adhesive particle is present in an amount effective to provide a reshapable ee effect.

A further aspect of the present invention provides a method of manufacturing a hair styling composition comprising including, in a hair styling composition at least one adhesive particle, as set forth above. In one embodiment, the at least one adhesive particle is present in an amount effective to provide a reshapable effect.

The determination of whether the at least one adhesive particle can provide a reshapable hair styling effect can be determined by an in vivo test. Specifically, a composition is prepared comprising the at least one adhesive particle and a cosmetically acceptable medium. The medium may be chosen, for example, from water, lower alcohols such as ethanol, and mixtures thereof. The composition typically comprises from about 1% to about 12% by weight active material. The compositions may be in any form noted above, including lotions.

Where the composition is in the form of a lotion, for example, the in vivo test proceeds as follows. The hair of the model is washed and then divided into two symmetrical portions, the right and the left sides. The composition is applied to one side of the head of the model, while a reference composition is applied to the other side of the head. The reference composition may, for example, be chosen from water, an existing commercial product, or another composition under study. The hairdresser dries and styles both sides of the head. The two sides of the head are separately evaluated for the styling effect, the cosmetic properties, and the reshapable effect. For example, once dried, the hair is brushed in different directions to remove the original styling. The hair is then brushed to either restore the original styling or to modify to form a new hair styling. The process of removing the styling, restoring/modifying the styling, and evaluating the success of restoring/modifying the styling is repeated at least one more time to determine whether the composition is a reshapable hair styling composition. A reshapable hair styling composition permits (1) the original hair styling to be restored after brushing and (2) the creation of a new hair styling after brushing, which may also be restored after brushing. If the composition to be evaluated is in another form, such as a shampoo or conditioner, the in vivo test can be appropriately modified by one skilled in the art.

It is understood that the person skilled in the art would recognize that not all formulations would provide reshapable effect for all hair types during in vivo testing and will know how to formulate and evaluate reshapable hair styling composition in view of the various hair parameters, such as length (short versus long), diameter (thin versus thick), structure (curly versus straight), condition (oily, dry, or normal); and whether the hair is colored, bleached, permed, or straightened. Thus, in vivo testing may require testing on 10–20 different individuals.

The invention may be understood more clearly with the aid of the non limiting examples which follow, and which constitutes an advantageous embodiment of the compositions in accordance with the invention.

EXAMPLES

Example 1

Styling Gel

A styling gel was formulated by mixing the following ingredients:

| Ingredient | Weight |
| --- | --- |
| Adhesive microspheres (Gel-Tac100B microspheres from API Company) | 1 g |
| Cross linked polyacrylic acid as thickening agent (Carbopol 980 from BF Goodrich Company) | 1.5 g |
| Amino Methyl Propanol | qsp pH 7 |
| Water | qsp 100 g |

Using the procedure described above, $F_{max}$ of the adhesive microspheres, an adhesive coated substrate, was measured to be 6.6 N. The size of the adhesive microspheres was 45 microns.

The resulting composition, upon application to hair, demonstrated good hold and styling properties and provided a reshapable effect.

Example 2

Pump Spray for Styling

A pump spray styling composition was formulated by mixing the following ingredients:

| Ingredient | Weight |
| --- | --- |
| Adhesive microspheres (Gel-Tac100B microspheres from API Company) | 10 g |
| Water | qsp 100 g |

Using the procedure described above, $F_{max}$ of the adhesive microspheres, an adhesive coated substrate, was measured to be 6.6 N. The size of the adhesive microspheres was 45 microns.

The resulting composition, upon application to hair, demonstrated good hold and styling properties and provided a reshapable effect.

Example 3

Styling Gel

A styling gel was formulated by mixing the following ingredients.

| Ingredient | Weight |
| --- | --- |
| Adhesive microspheres (Gel-Tac100B microspheres from API Company) | 5 g |
| Guar hydroxypropyltrimonium chloride (Jaguar 13S from Rhodia Company) | 2 g |
| Water | qsp 100 g |

Using the procedure described above, $F_{max}$ of the adhesive microspheres, an adhesive coated substrate, was measured to be 6.6 N. The size of the adhesive microspheres was 45 microns.

The resulting composition, upon application to hair, demonstrated good hold and styling properties and provided a reshapable effect.

What is claimed is:

1. A hair styling composition comprising at least one adhesive particle,
wherein said at least one adhesive particle comprises at least one substrate and an at least partial coating, wherein said at least partial coating comprises at least one adhesive,
wherein said at least one substrate and said at least partial coating are not the same, and
wherein said at least one adhesive particle has a mean length greater than 1 micron.

2. The hair styling composition according to claim 1, further comprising a cosmetically acceptable carrier.

3. The hair styling composition according to claim 1, wherein said at least one adhesive particle is present in an amount effective to provide a holding effect.

4. The hair styling composition according to claim 1, wherein said at least one substrate is chosen from adhesives, polymeric materials, metal alloys, metal oxides, ceramics, and glasses.

5. The hair styling composition according to claim 4, wherein said at least one substrate is an adhesive chosen from polymeric adhesives.

6. The hair styling composition according to claim 1, wherein said at least one adhesive is chosen from polymeric adhesives.

7. The hair styling composition according to claim 3, wherein said at least one adhesive particle has an $F_{max}$ greater than about 0.5 N.

8. The hair styling composition according to claim 3, wherein said at least one adhesive particle has an $F_{max}$ greater than about 1N.

9. The hair styling composition according to claim 3, wherein said at least one adhesive particle has an $F_{max}$ greater than about 4N.

10. The hair styling composition according to claim 3, wherein said at least one adhesive particle has an $E_s$ less than about 300 µJ.

11. The hair styling composition according to claim 5, wherein said polymeric adhesives are chosen from (meth) acrylic copolymers comprising: (a) units derived from at least one monomer present at from about 0.1% to about 99% by weight and (b) units derived from at least one co-monomer present at up to about 99.9% by weight of the total weight of the polymer.

12. The hair styling composition according to claim 11, wherein the at least one monomer recited in (a) is represented by formula:

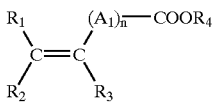

wherein n is an integer ranging from 0 to 10; $A_1$ denotes a methylene group and when n is greater than 1, each $A_1$ is independently represented by —LCH$_2$—, where L is chosen from a valency bond and heteroatoms; $R_1$ is ch osen from hydrogen, phenyl groups, and benzyl groups; $R_2$ is chosen from hydrogen, lower alkyl groups, and carboxyl groups; and $R_3$ i s chosen from hydrogen, lower alkyl groups, —CH$_2$—COOH groups, phenyl groups, and benzyl groups; and $R_4$ is chosen from hydrogen, $C_1$ to $C_{18}$ alkyls, $C_2$ to $C_8$ alkoxyalkyls, $C_2$ to $C_8$ alkylthioalkyls, and $C_2$ to $C_8$ cyanoalkyls.

13. The hair styling composition according to claim 11, wherein said (meth)acrylic copolymers further comprise (c) units derived from at least one vinylidene co-monomer containing at least one group chosen from carboxyl and hydroxyl groups present at from about 1% to about 10% by weight of the total weight of the polymer.

14. The hair styling composition according to claim 6, wherein said polymeric adhesives are chosen from (meth) acrylic copolymers comprising: (a) units derived from at least one monomer present at from about 0.1% to about 99% by weight and (b) units derived from at least one co-monomer present at up to about 99.9% by weight of the total weight of the polymer.

15. The hair styling composition according to claim 14, wherein the at least one monomer recited in (a) is represented by formula:

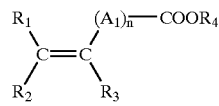

wherein n is an integer ranging from 0 to 10; $A_1$ denotes a methylene group and when n is greater than 1, each $A_1$ is independently represented by —LCH$_2$—, where L is chosen from a valency bond and heteroatoms; $R_1$ is chosen from hydrogen, phenyl groups, and benzyl groups; $R_2$ is chosen from hydrogen, lower alkyl groups, and carboxyl groups; and $R_3$ is chosen from hydrogen, lower alkyl groups, —CH$_2$—COOH groups, phenyl groups, and benzyl groups; and $R_4$ is chosen from hydrogen, $C_1$ to $C_{18}$ alkyls, $C_2$ to $C_8$ alkoxyalkyls, $C_2$ to $C_8$ alkylthioalkyls, and $C_2$ to $C_8$ cyanoalkyls.

16. The hair styling composition according to claim 14, wherein said (meth)acrylic copolymers further comprise (c) units derived from at least one vinylidene co-monomer containing at least one group chosen from carboxyl and hydroxyl groups present at from about 1% to about 10% by weight of the total weight of the polymer.

17. The hair styling composition according to claim 5, wherein said polymeric adhesives are chosen from anionic, nonionic, cationic, and amphoteric fixing polymers.

18. The hair styling composition according to claim 6, wherein said polymeric adhesives are chosen from anionic, nonionic, cationic, and amphoteric fixing polymers.

19. The hair styling composition according to claim 4, wherein said at least one substrate is adhesive and wherein said at least partial coating comprises at least one adhesive, which is different from the at least one substrate.

20. The hair styling composition according to claim 1, wherein said at least one adhesive particle has a shape chosen from spherical, spheroidal, rod-like, platelet-like, flake-like, and irregular shapes.

21. The hair styling composition according to claim 1, wherein the mean length of said at least one adhesive particle ranges from about 5 microns to about 1000 microns.

22. The hair styling composition according to claim 21, wherein the mean length of said at least one adhesive particle ranges from about 10 microns to about 100 microns.

23. The hair styling composition according to claim 1, wherein said at least one adhesive particle has a ratio of length to width greater than or equal to about 1:1.

24. The hair styling composition according to claim 1, wherein said at least one adhesive particle is present in said composition at a concentration ranging from about 0.1% to about 50% relative to the total weight of said composition.

25. The hair styling composition according to claim 1, further comprising at least one additive chosen from conditioning agents; reducing agents; silanes; fatty substances; thickeners; anti-foaming agents; hydrating agents; fillers; sunscreens; active haircare agents; perfumes; preservatives; cationic, anionic, nonionic, and amphoteric surfactants; cationic, anionic, nonionic, and amphoteric polymers; polyols; proteins; provitamins; vitamins; dyes; tints; bleaches; and pH adjusting agents.

26. A hair styling composition comprising, in a cosmetically acceptable carrier, at least one adhesive particle,
    wherein said at least one adhesive particle comprises at least one substrate and an at least partial coating, wherein said at least partial coating comprises at least one adhesive,
    wherein said at least one substrate and said at least partial coating are not the same,
    wherein said at least one adhesive particle has a mean length greater than 1 micron, and
    wherein the hair styling composition is in a form chosen from sprays, aerosols, mousses, gels, muds, sticks, and lotions.

27. An aerosol device comprising a vessel, which comprises
    (1) an aerosol composition, which comprises
        a liquid phase comprising, in a cosmetically acceptable carrier, at least one composition comprising at least one adhesive particle, wherein said at least one adhesive particle comprises at least one substrate and an at least partial coating, wherein said at least partial coating comprises at least one adhesive, wherein said at least one substrate and said at least partial coating are not the same, and wherein said at least one adhesive particle has a mean length greater than 1 micron, and
        a propellant, and
    (2) a dispenser.

28. A method of cosmetically treating hair, comprising applying to the hair before, during, or after shaping of the hairstyle a hair styling composition, which comprises, in a cosmetically acceptable carrier, at least one adhesive particle,
    wherein said at least one adhesive particle comprises at least one substrate and an at least partial coating, wherein said at least partial coating comprises at least one adhesive,
    wherein said at least one substrate and said at least partial coating are not the same, and
    wherein said at least one adhesive particle has a mean length greater than 1 micron.

29. A method of manufacturing a hair styling composition comprising including at least one adhesive particle in a hair styling composition,
    wherein said at least one adhesive particle comprises at least one substrate and an at least partial coating, wherein said at least partial coating comprises at least one adhesive,
    wherein said at least one substrate and said at least partial coating are not the same, and
    wherein said at least one adhesive particle has a mean length greater than 1 micron.

30. A method for providing a holding effect to hair, comprising applying to the hair a composition comprising, in a cosmetically acceptable carrier, at least one adhesive particle, wherein said at least one adhesive particle comprises at least one substrate and an at least partial coating, wherein said at least partial coating comprises at least one adhesive, wherein said at least one substrate and said at least partial coating are not the same, and wherein said at least one adhesive particle has a mean length greater than 1 micron and is present in an amount effective to provide a holding effect.

31. A reshapable hair styling composition comprising at least one adhesive particle,
    wherein said at least one adhesive particle comprises at least one substrate and an at least partial coating, wherein said at least partial coating comprises at least one adhesive,
    wherein said at least one substrate and said at least partial coating are not the same,
    wherein said at least one adhesive particle has a mean length greater than 1 micron, and
    wherein said at least one adhesive particle is present in an amount effective to provide a reshapable effect.

32. The reshapable hair styling composition according to claim 31, further comprising a cosmetically acceptable carrier.

33. The reshapable hair styling composition according to claim 31, wherein said at least one substrate is chosen from adhesives, polymeric materials, metal alloys, metal oxides, ceramics, and glasses.

34. The reshapable hair styling composition according to claim 33, wherein said at least one substrate is an adhesive chosen from polymeric adhesives.

35. The reshapable hair styling composition according to claim 31, wherein said at least one adhesive is chosen from polymeric adhesives.

36. The reshapable hair styling composition according to claim 31, wherein said at least one adhesive particle has an $F_{max}$ greater than about 0.5 N.

37. The reshapable hair styling composition according to claim 31, wherein said at least one adhesive particle has an $F_{max}$ greater than about 1N.

38. The reshapable hair styling composition according to claim 31, wherein said at least one adhesive particle has an $F_{max}$ greater than about 4N.

39. The reshapable hair styling composition according to claim 31, wherein said at least one adhesive particle has an $E_s$ less than about 300 $\mu$J.

40. The reshapable hair styling composition according to claim 34, wherein said polymeric adhesives are chosen from (meth)acrylic copolymers comprising: (a) units derived from at least one monomer present at from about 0.1% to about 99% by weight and (b) units derived from at least one co-monomer present at up to about 99.9% by weight of the total weight of the polymer.

41. The reshapable hair styling composition according to claim 40, wherein the at least one monomer recited in (a) is represented by formula:

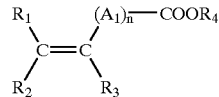

wherein n is an integer ranging from 0 to 10; $A_1$ denotes a methylene group and when n is greater than 1, each $A_1$ is independently represented by —$LCH_2$—, where L is chosen from a valency bond and heteroatoms; $R_1$ is chosen from hydrogen, phenyl groups, and benzyl groups; $R_2$ is chosen from hydrogen, lower alkyl groups, and carboxyl groups; and $R_3$ is chosen from hydrogen, lower alkyl groups, —$CH_2$—COOH groups, phenyl groups, and benzyl groups;

and $R_4$ is chosen from hydrogen, $C_1$ to $C_{18}$ alkyls, $C_2$ to $C_8$ alkoxyalkyls, $C_2$ to $C_8$ alkylthioalkyls, and $C_2$ to $C_8$ cyanoalkyls.

42. The reshapable hair styling composition according to claim 40, wherein said (meth)acrylic copolymers further comprise (c) units derived from at least one vinylidene co-monomer containing at least one group chosen from carboxyl and hydroxyl groups present at from about 1% to about 10% by weight of the total weight of the polymer.

43. The reshapable hair styling composition according to claim 35, wherein said polymeric adhesives are chosen from (meth)acrylic copolymers comprising: (a) units derived from at least one monomer present at from about 0.1% to about 99% by weight and (b) units derived from at least one co-monomer present at up to about 99.9% by weight of the total weight of the polymer.

44. The reshapable hair styling composition according to claim 43, wherein the at least one monomer recited in (a) is represented by formula:

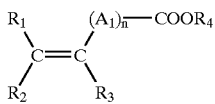

wherein n is an integer ranging from 0 to 10; $A_1$ denotes a methylene group and when n is greater than 1, each $A_1$ is independently represented by —$LCH_2$—, where L is chosen from a valency bond and heteroatoms; $R_1$ is chosen from hydrogen, phenyl groups, and benzyl groups; $R_2$ is chosen from hydrogen, lower alkyl groups, and carboxyl groups; and $R_3$ is chosen from hydrogen, lower alkyl groups, —$CH_2$—COOH groups, phenyl groups, and benzyl groups; and $R_4$ is chosen from hydrogen, $C_1$ to $C_{18}$ alkyls, $C_2$ to $C_8$ alkoxyalkyls, $C_2$ to $C_8$ alkylthioalkyls, and $C_2$ to $C_8$ cyanoalkyls.

45. The reshapable hair styling composition according to claim 43, wherein said (meth)acrylic copolymers further comprise (c) units derived from at least one vinylidene co-monomer containing at least one group chosen from carboxyl and hydroxyl groups present at from about 1% to about 10% by weight of the total weight of the polymer.

46. The reshapable hair styling composition according to claim 34, wherein said polymeric adhesives are chosen from anionic, nonionic, cationic, and amphoteric fixing polymers.

47. The reshapable hair styling composition according to claim 35, wherein said polymeric adhesives are chosen from anionic, nonionic, cationic, and amphoteric fixing polymers.

48. The reshapable hair styling composition according to claim 33, wherein said at least one substrate is adhesive and wherein said at least partial coating comprises at least one adhesive, which is different from the at least one substrate.

49. The reshapable hair styling composition according to claim 31, wherein said at least one adhesive particle has a shape chosen from spherical, spheroidal, rod-like, platelet-like, flake-like, and irregular shapes.

50. The reshapable hair styling composition according to claim 31, wherein the mean length of said at least one adhesive particle ranges from about 5 microns to about 1000 microns.

51. The reshapable hair styling composition according to claim 50, wherein the mean length of said at least one adhesive particle ranges from about 10 microns to about 100 microns.

52. The reshapable hair styling composition according to claim 31, wherein said at least one adhesive particle has a ratio of length to width greater than or equal to about 1:1.

53. The reshapable hair styling composition according to claim 31, wherein said at least one adhesive particle is present in said composition at a concentration ranging from about 0.1% to about 50% relative to the total weight of said composition.

54. The reshapable hair styling composition according to claim 31, further comprising at least one additive chosen from conditioning agents; reducing agents; silanes; fatty substances; thickeners; anti-foaming agents; hydrating agents; fillers; sunscreens; active haircare agents; perfumes; preservatives; cationic, anionic, nonionic, and amphoteric surfactants; cationic, anionic, nonionic, and amphoteric polymers; polyols; proteins; provitamins; vitamins; dyes; tints; bleaches; and pH adjusting agents.

55. A reshapable hair styling composition comprising, in a cosmetically acceptable carrier, at least one adhesive particle,
wherein said at least one adhesive particle comprises at least one substrate and an at least partial coating, wherein said at least partial coating comprises at least one adhesive,
wherein said at least one substrate and said at least partial coating are not the same,
wherein said at least one adhesive particle has a mean length greater than 1 micron,
wherein said at least one adhesive particle is present in an amount effective to provide a reshapable effect, and
wherein the hair styling composition is in a form chosen from sprays, aerosols, mousses, gels, muds, sticks, and lotions.

56. An aerosol device comprising a vessel, which comprises
(1) an aerosol composition, which comprises
a liquid phase comprising, in a cosmetically acceptable carrier, at least one composition comprising at least one adhesive particle, wherein said at least one adhesive particle comprises at least one substrate and an at least partial coating, wherein said at least partial coating comprises at least one adhesive, wherein said at least one substrate and said at least partial coating are not the same, wherein said at least one adhesive particle has a mean length greater than 1 micron, and wherein said at least one adhesive particle is present in an amount effective to provide a reshapable effect, and
a propellant, and
(2) a dispenser.

57. A method of cosmetically treating hair, comprising applying to the hair before, during, or after shaping of the hairstyle a reshapable hair styling composition, which comprises, in a cosmetically acceptable carrier, at least one adhesive particle,
wherein said at least one adhesive particle comprises at least one substrate and an at least partial coating, wherein said at least partial coating comprises at least one adhesive,
wherein said at least one substrate and said at least partial coating are not the same,
wherein said at least one adhesive particle has a mean length greater than 1 micron,
wherein said at least one adhesive particle is present in an amount effective to provide a reshapable effect.

58. A method of manufacturing a reshapable hair styling composition comprising including at least one adhesive particle in a hair styling composition, wherein said at least one adhesive particle comprises at least one substrate and an at least partial coating, wherein said at least partial coating comprises at least one adhesive, wherein said at least one substrate and said at least partial coating are not the same, wherein said at least one adhesive particle has a mean length greater than 1 micron, wherein said at least one adhesive particle is present in an amount effective to provide a reshapable effect.

59. A method of reshaping hair, comprising (a) applying to the hair a composition comprising, in a cosmetically acceptable carrier, at least one adhesive particle, wherein said at least one adhesive particle comprises at least one substrate and an at least partial coating, wherein said at least partial coating comprises at least one adhesive,
   wherein said at least one substrate and said at least partial coating are not the same,
   wherein said at least one adhesive particle has a mean length greater than 1 micron,
   wherein said at least one adhesive particle is present in an amount effective to provide a reshapable effect, and (b) thereafter shaping the hairstyle at least once, wherein no additional composition or heat is added.

60. A hair styling composition comprising at least one adhesive particle,
   wherein said at least one adhesive particle comprises at least one substrate and an at least partial coating, wherein said at least partial coating comprises at least one adhesive,
   wherein said at least one substrate and said at least partial coating are not the same, and
   wherein said at least one adhesive particle has a mean length greater than 1 micron as determined by optical microscopy.

61. A hair styling composition comprising, in a cosmetically acceptable carrier, at least one adhesive particle,
   wherein said at least one adhesive particle comprises at least one substrate and an at least partial coating, wherein said at least partial coating comprises at least one adhesive,
   wherein said at least one substrate and said at least partial coating are not the same,
   wherein said at least one adhesive particle has a mean length greater than 1 micron as determined by optical microscopy, and
   wherein the hair styling composition is in a form chosen from sprays, aerosols, mousses, gels, muds, sticks, and lotions.

62. An aerosol device comprising a vessel, which comprises (1) an aerosol composition, which comprises
   a liquid phase comprising, in a cosmetically acceptable carrier, at least one composition comprising at least one adhesive particle, wherein said at least one adhesive particle comprises at least one substrate and an at least partial coating, wherein said at least partial coating comprises at least one adhesive, wherein said at least one substrate and said at least partial coating are not the same, and wherein said at least one adhesive particle has a mean length greater than 1 micron as determined by optical microscopy, and
   a propellant, and (2) a dispenser.

63. A method of cosmetically treating hair, comprising applying to the hair before, during, or after shaping of the hairstyle a hair styling composition, which comprises, in a cosmetically acceptable carrier, at least one adhesive particle,
   wherein said at least one adhesive particle comprises at least one substrate and an at least partial coating, wherein said at least partial coating comprises at least one adhesive,
   wherein said at least one substrate and said at least partial coating are not the same, and
   wherein said at least one adhesive particle has a mean length greater than 1 micron as determined by optical microscopy.

64. A method of manufacturing a hair styling composition comprising including at least one adhesive particle in a hair styling composition,
   wherein said at least one adhesive particle comprises at least one substrate and an at least partial coating, wherein said at least partial coating comprises at least one adhesive,
   wherein said at least one substrate and said at least partial coating are not the same, and
   wherein said at least one adhesive particle has a mean length greater than 1 micron as determined by optical microscopy.

65. A method for providing a holding effect to hair, comprising applying to the hair a composition comprising, in a cosmetically acceptable carrier, at least one adhesive particle, wherein said at least one adhesive particle comprises at least one substrate and an at least partial coating, wherein said at least partial coating comprises at least one adhesive, wherein said at least one substrate and said at least partial coating are not the same, and wherein said at least one adhesive particle has a mean length greater than 1 micron as determined by optical microscopy and is present in an amount effective to provide a holding effect.

66. A reshapable hair styling composition comprising at least one adhesive particle,
   wherein said at least one adhesive particle comprises at least one substrate and an at least partial coating, wherein said at least partial coating comprises at least one adhesive,
   wherein said at least one substrate and said at least partial coating are not the same,
   wherein said at least one adhesive particle has a mean length greater than 1 micron as determined by optical microscopy, and
   wherein said at least one adhesive particle is present in an amount effective to provide a reshapable effect.

67. A reshapable hair styling composition comprising, in a cosmetically acceptable carrier, at least one adhesive particle,
   wherein said at least one adhesive particle comprises at least one substrate and an at least partial coating, wherein said at least partial coating comprises at least one adhesive,
   wherein said at least one substrate and said at least partial coating are not the same,
   wherein said at least one adhesive particle has a mean length greater than 1 micron as determined by optical microscopy, wherein said at least one adhesive particle is present in an amount effective to provide a reshapable effect, and wherein the hair styling composition is in a form chosen from sprays, aerosols, mousses, gels, muds, sticks, and lotions.

68. An aerosol device comprising a vessel, which comprises (1) an aerosol composition, which comprises a liquid phase comprising, in a cosmetically acceptable carrier, at least one composition comprising at least one adhesive particle, wherein said at least one adhesive particle comprises at least one substrate and an at least partial coating, wherein said at least partial coating comprises at least one adhesive, wherein said at least one substrate and said at least partial coating are not the same, wherein said at least one adhesive particle has a mean length greater than 1 micron as determined by optical microscopy, and wherein said at least one adhesive particle is present in an amount effective to provide a reshapable effect, and a propellant, and (2) a dispenser.

69. A method of cosmetically treating hair, comprising applying to the hair before, during, or after shaping of the hairstyle a reshapable hair styling composition, which comprises, in a cosmetically acceptable carrier, at least one adhesive particle, wherein said at least one adhesive particle comprises at least one substrate and an at least partial coating, wherein said at least partial coating comprises at least one adhesive, wherein said at least one substrate and said at least partial coating are not the same, wherein said at least one adhesive particle has a mean length greater than 1 micron as determined by optical microscopy, wherein said at least one adhesive particle is present in an amount effective to provide a reshapable effect.

70. A method of manufacturing a reshapable hair styling composition comprising including at least one adhesive particle in a hair styling composition, wherein said at least one adhesive particle comprises at least one substrate and an at least partial coating, wherein said at least partial coating comprises at least one adhesive, wherein said at least one substrate and said at least partial coating are not the same, wherein said at least one adhesive particle has a mean length greater than 1 micron as determined by optical microscopy, wherein said at least one adhesive particle is present in an amount effective to provide a reshapable effect.

71. A method of reshaping hair, comprising (a) applying to the hair a composition comprising, in a cosmetically acceptable carrier, at least one adhesive particle, wherein said at least one adhesive particle comprises at least one substrate and an at least partial coating, wherein said at least partial coating comprises at least one adhesive, wherein said at least one substrate and said at least partial coating are not the same, wherein said at least one adhesive particle has a mean length greater than 1 micron as determined by optical microscopy, wherein said at least one adhesive particle is present in an amount effective to provide a reshapable effect, and (b) thereafter shaping the hairstyle at least once, wherein no additional composition or heat is added.

* * * * *